(12) United States Patent
Han et al.

(10) Patent No.: US 10,213,769 B2
(45) Date of Patent: Feb. 26, 2019

(54) METHOD FOR PRODUCING HYDROCARBON DEHYDROGENATION CATALYST USING SPONGE-TYPE SUPPORT

(71) Applicant: Heesung Catalysts Corporation, Siheung-si (KR)

(72) Inventors: Hyun-sik Han, Seoul (KR); Young-San Yoo, Siheung-Si (KR); Ho-Dong Kim, Namyangju-si (KR)

(73) Assignee: HEESUNG CATALYSTS CORPORATION (KR)

( * ) Notice: Subject to any disclaimer, the term of this patent is extended or adjusted under 35 U.S.C. 154(b) by 0 days.

(21) Appl. No.: 15/101,876

(22) PCT Filed: Dec. 3, 2014

(86) PCT No.: PCT/KR2014/011739
§ 371 (c)(1),
(2) Date: Jun. 3, 2016

(87) PCT Pub. No.: WO2015/084041
PCT Pub. Date: Jun. 11, 2015

(65) Prior Publication Data
US 2017/0001174 A1    Jan. 5, 2017

(30) Foreign Application Priority Data
Dec. 4, 2013 (KR) ........................ 10-2013-0149680

(51) Int. Cl.
*B01J 23/62* (2006.01)
*B01J 21/04* (2006.01)
(Continued)

(52) U.S. Cl.
CPC ............. *B01J 23/626* (2013.01); *B01J 21/04* (2013.01); *B01J 23/14* (2013.01); *B01J 23/42* (2013.01);
(Continued)

(58) Field of Classification Search
CPC ...... B01J 21/04; B01J 23/626; B01J 35/1014; B01J 35/1038; B01J 35/1042;
(Continued)

(56) References Cited

U.S. PATENT DOCUMENTS 8,993,474 B2    3/2015 Choi et al.
2002/0198428 A1*    12/2002 Iezzi ...................... B01J 8/0055
585/654

(Continued)

FOREIGN PATENT DOCUMENTS

| KR | 10-2007-0075064 A | 7/2007 |
| KR | 10-2010-0078465 A | 7/2010 |
| KR | 10-2011-0109625 A | 10/2011 |

OTHER PUBLICATIONS

Tokudome , Synthesis of Monolithic Al2O3 with Well-defined Macropores and Mesostructured Skeletons via the Sol-Gel Process Accompanied by Phase Separation, Chem. Mater., 19: 3393-3398, Jun. 2007.*

(Continued)

*Primary Examiner* — Jun Li
(74) *Attorney, Agent, or Firm* — Fish IP Law, LLP

(57) ABSTRACT

Disclosed are a catalyst for dehydrogenating a paraffinic hydrocarbon and a method of preparing the same, wherein the catalyst is configured such that a sponge-type alumina support having 3D meso/macro pores is directly impregnated with an active metal, thus decreasing the diffusion resistance of a material, realizing structural stability, and maximizing the distribution of the active metal in the support, thereby significantly increasing olefin conversion and selectivity. In this catalyst, the sponge-type alumina support is directly impregnated with the active metal to thus form an active metal layer inside the support having 3D meso/macro pores that are interconnected to each other.

4 Claims, 3 Drawing Sheets

(51) Int. Cl.

| | |
|---|---|
| *B01J 37/08* | (2006.01) |
| *B01J 37/16* | (2006.01) |
| *B01J 23/14* | (2006.01) |
| *B01J 23/42* | (2006.01) |
| *B01J 35/10* | (2006.01) |
| *C10G 45/62* | (2006.01) |
| *C07C 5/333* | (2006.01) |
| *B01J 37/02* | (2006.01) |
| *B01J 35/04* | (2006.01) |

(52) U.S. Cl.
CPC ......... *B01J 35/109* (2013.01); *B01J 35/1014* (2013.01); *B01J 35/1038* (2013.01); *B01J 35/1042* (2013.01); *B01J 35/1061* (2013.01); *B01J 35/1066* (2013.01); *B01J 37/08* (2013.01); *B01J 37/16* (2013.01); *C07C 5/3337* (2013.01); *C10G 45/62* (2013.01); *B01J 35/04* (2013.01); *B01J 37/0207* (2013.01); *B01J 37/0236* (2013.01); *C07C 2521/04* (2013.01); *C07C 2523/62* (2013.01)

(58) Field of Classification Search
CPC .... B01J 37/0207; B01J 37/0236; B01J 37/08; B01J 37/16; C07C 5/3337; C07C 2521/04; C07C 2523/62
See application file for complete search history.

(56) References Cited

U.S. PATENT DOCUMENTS

2003/0191351 A1* 10/2003 Voskoboynikov ....... B01J 21/04
585/660
2014/0378731 A1* 12/2014 Iezzi ....................... B01J 23/58
585/660

OTHER PUBLICATIONS

Cho, K.M., et al., "Effect of Calcination Temperature of Alumina Supports on the Wax Hydrocracking Performance of Pd-Loaded Mesoporous Alumina Xerogel Catalysts for the Production of Middle Distillate," Chemical Engineering Journal, No. 146 (2009) pp. 307-314.

ISA/KR, International Search Report for Int'l Appln No. PCT/KR2014/011739, dated Jan. 20, 2015, 2 pages.

* cited by examiner

DRAWINGS
[FIG. 1]
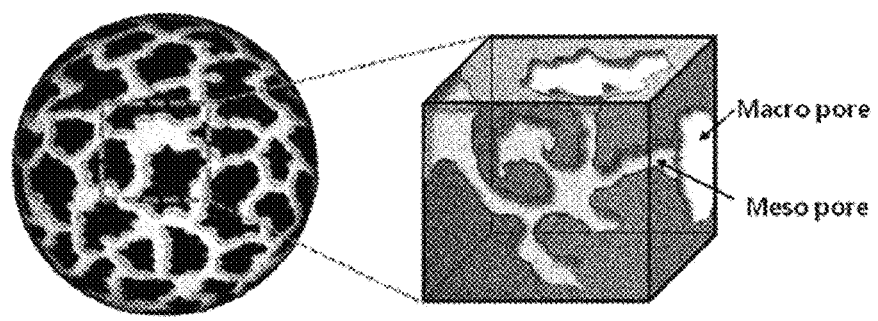

[FIG. 2]
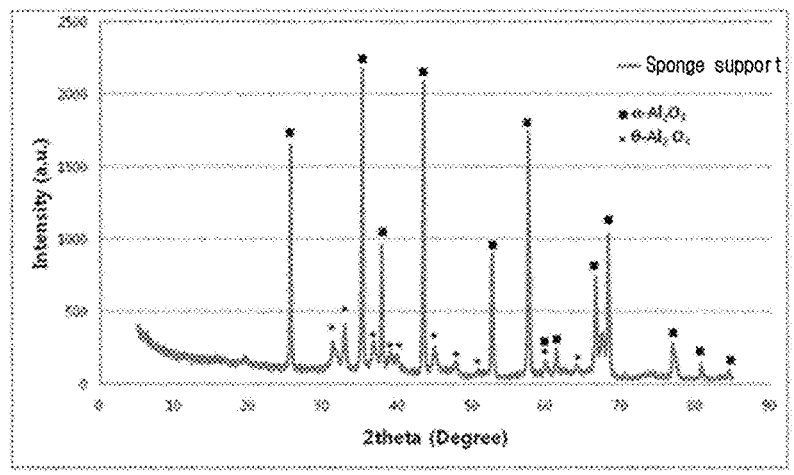
(a)
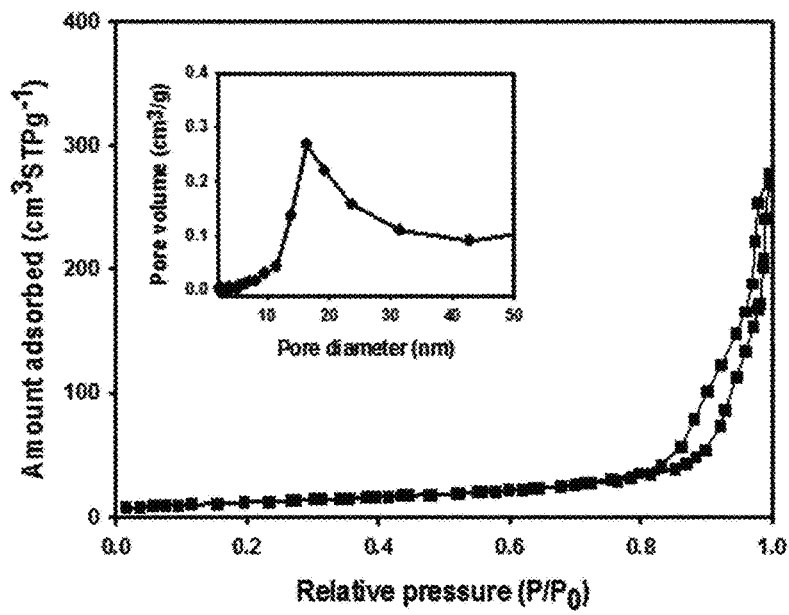
(b)

[FIG. 3]
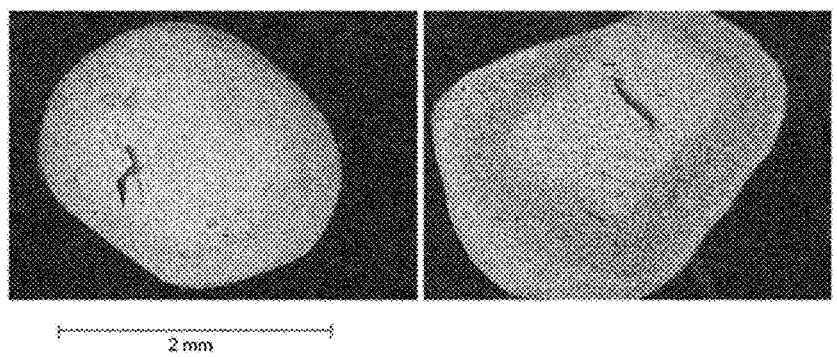

METHOD FOR PRODUCING HYDROCARBON DEHYDROGENATION CATALYST USING SPONGE-TYPE SUPPORT

TECHNICAL FIELD

The present invention relates to a hydrocarbon dehydrogenation catalyst using a sponge-type support and a method of preparing the same, particularly to a catalyst for selectively dehydrogenating a paraffinic hydrocarbon and a method of preparing the same, and more particularly to the preparation of a dehydrogenation catalyst exhibiting increased olefin conversion and selectivity using the structural properties of a sponge-type alumina support having three-dimensional (3D) meso/macro pores.

BACKGROUND ART

Typically, a linear olefin having 9 or more carbon atoms, which is to be dehydrogenated, is a valued compound that is widely utilized as a basic material for intermediates for preparing biodegradable detergents, medicines, plastics, synthetic rubber and the like. Methods of producing linear olefin from linear paraffin having 9 to 13 or more carbon atoms through dehydrogenation are known, and generally include bringing hydrogen and gaseous paraffin into contact with a dehydrogenation catalyst, followed by reaction at a high temperature under atmospheric pressure. In the dehydrogenation reaction system, the catalyst has been prepared to mainly increase the rate of reaction and simultaneously inhibit side reactions such as pyrolysis, coke production, isomerization, etc. so as to increase the linear olefin selectivity.

A dehydrogenation catalyst, which is commonly useful for producing linear olefin from linear paraffin, is mainly prepared by impregnating silica, alumina, or silica-alumina with a Group VIII precious metal such as platinum or the like. Such a catalyst is problematic because metal particles may be sintered early due to the high temperature in the initial stage of the reaction, undesirably shortening the lifetime of the catalyst. In order to increase the activity of the catalyst for dehydrogenating linear paraffin, the olefin selectivity, and the lifetime of the catalyst, useful is a catalyst configured such that a Group VIII precious metal such as platinum or the like is coupled with one or more other metals selected from among tin, lithium, potassium, sodium, etc. Meanwhile, in the reaction mechanism for dehydrogenating a paraffinic hydrocarbon, the reaction progresses at a high temperature, and thus, not only the dehydrogenation reaction but also side reactions such as pyrolysis and coke production may occur, undesirably lowering catalytic activity and selectivity. Particularly in the case of a catalyst configured such that the active metal is deeply incorporated into the support, total dispersibility becomes good, and thus, even when the reactant is incorporated into the support through material transfer and diffusion, it comes into contact with the active metal sites, thus increasing the total activity. However, the reactant or product may reside in the catalyst for an excessively long period of time, undesirably causing side reactions such as adsorption of the product inside the catalyst, additional reaction of products, isomerization and coke production, and shortening the lifetime of the catalyst. Hence, thorough research is ongoing into distribution of the active metal inside the support to suppress side reactions in the dehydrogenation reaction and to increase the produced olefin selectivity. In particular, there are proposed methods for disposing the active metal on the outer surface of the catalyst support to minimize the material transfer effect, and to increase the selectivity and maximize the activity while minimizing the contact time between the reactant and the catalyst.

For example, U.S. Pat. Nos. 4,077,912 and 4,255,253 disclose a catalyst prepared by coating a support with a catalytic metal oxide, thus enabling incorporation to the outer surface of the support, and U.S. Pat. No. 6,177,381 discloses a catalyst where, in order to prevent the diffusion of an active metal into the support upon loading of the active metal, alpha alumina and cordierite are used as the inner core, and gamma alumina and active metal are mixed to give a slurry which is then used to form an outer layer, thereby increasing the selectivity and the extent of dehydrogenation using the catalyst. The above patent also discloses that the slurry for forming the outer layer is mixed together with the active metal, after which the resulting mixture may be applied on the inner core, or alternatively that the slurry may be applied and the active metal may then be loaded thereon.

DISCLOSURE

Technical Problem

However, such a multilayered catalyst having a core-shell configuration is problematic because the core and the shell are separately manufactured and thus the manufacturing process is complicated, and also because the density of the support is increased due to the use of the fired alpha alumina or cordierite as the support, and high manufacturing costs may result. Furthermore, the slurry for the shell is unfavorable in that interlayer loss may occur upon friction in the catalyst, compared to monolithic spherical support catalysts. Although an organic or inorganic binder is used to attach the inner core and the outer layer in the manufacture of the multilayered catalyst, the organic binder for preventing the outer layer from being stripped may decrease the surface area of the outer layer due to thermal impact resulting from heat of the dehydrogenation reaction, and the inorganic binder may decrease the number of active reaction sites on the outer layer.

Technical Solution

The present invention provides a catalyst for dehydrogenating a paraffinic hydrocarbon and a method of preparing the same, wherein the catalyst is configured such that a sponge-type alumina support having 3D meso/macro pores is directly impregnated with an active metal, thus decreasing the diffusion resistance of a material, realizing structural stability, and maximizing the distribution of the active metal in the support, ultimately significantly increasing olefin conversion and selectivity.

The present inventors have recognized the fact that the direct impregnation of a spherical support with an active metal makes it impossible to control the characteristics of the outer layer of the support due to the diffusion of the active metal into the porous support, and have manufactured a catalyst configured such that a support, which has an enlarged pore structure so as to facilitate the material transfer of a reactant and the diffusion thereof, unlike typical alumina supports, is directly impregnated with an active metal, and thus the active metal is uniformly distributed inside the support.

Accordingly, the present invention provides a method of preparing a dehydrogenation catalyst, in which the catalyst is configured such that a sponge-type alumina support is directly impregnated with an active metal to thus form an active metal layer inside the support having 3D meso/macro pores that are interconnected to each other.

Advantageous Effects

According to the present invention, the catalyst includes a sponge-type alumina support having a 3D pore network to thus enable the uniform distribution of active metals for a catalyst inside the support, thus suppressing side reactions, decreasing the diffusion resistance of the reactant due to the large pore size of the support, and shortening the retention time of the reactant and the product in the support, thereby increasing the conversion efficiency and selectivity in the catalytic reaction. Further, the catalyst prepared according to the present invention is favorable because the support itself is impregnated with the active metal, thus inhibiting the stripping of the active material and exhibiting high strength and thus superior durability compared to conventional multilayered catalysts, ultimately generating economic benefits.

DESCRIPTION OF DRAWINGS

FIG. 1 illustrates the configuration of a sponge-type support having 3D meso/macro pores according to the present invention;

FIGS. 2(a) and 2(b) are respective graphs illustrating the results of X-ray diffraction (XRD) and nitrogen physical adsorption isotherm of the sponge-type support having 3D meso/macro pores according to the present invention, wherein the specific surface area of a material, total pore volume, and pore size are measured through nitrogen physical adsorption; and FIG. 3 illustrates video microscopy images of the catalyst prepared using the sponge-type support having 3D meso/macro pores according to the present invention.

BEST MODE

The present invention addresses a method of preparing a catalyst, which includes impregnating a sponge-type alumina support having a 3D pore network with a dehydrogenation composite metal active component, whereby the catalyst retains its activity while exhibiting increased reaction selectivity, is effective at avoiding deactivation due to the production of coke, is resistant to external impacts due to its high strength, and shows no changes in the properties of the active material due to heat. More specifically, the present invention addresses a method of preparing a dehydrogenation catalyst, wherein, in order to solve problems with a conventional dehydrogenation catalyst, including coke deposition in a catalyst and low catalytic activity, a sponge-type alumina support having a large pore size is directly impregnated with an active metal, whereby the active metal is effectively dispersed inside the support, thus decreasing the diffusion resistance of the reactant inside the support and increasing the material transfer rate, resulting in increased conversion efficiency, and furthermore, the olefin selectivity and conversion may be remarkably raised due to the short contact time between the catalyst and the reactant. In the present invention, the active metal layer formed on the outer surface of the support is different from the active (metal) outer layer of a conventional core-shell-type catalyst, because slurry is not additionally applied, but active metal components are directly loaded into the 3D pores of the support.

According to the present invention, the method of preparing the catalyst using the sponge-type support includes:
providing an alumina support having meso/macro pore sizes;
thermally treating the support at 800 to 1200° C. for 2 to 10 hr in an air atmosphere;
dispersing an active metal precursor comprising platinum, tin, an alkali metal or an alkaline earth metal in the support so as to be loaded into the support;
drying the support having the loaded active metal at 80 to 150° C.;
thermally treating the dried catalyst at 400 to 700° C. for 2 to 10 hr in an air atmosphere; and
reducing the thermally treated catalyst at 400 to 700° C. for 1 to 10 hr in a hydrogen atmosphere.

Unlike a typically useful alumina support having a specific surface area of 200 $m^2/g$ or more, a total pore volume of 0.5 to 2.0 $cm^3/g$, and a pore size of 5 to 20 nm, the sponge-type support according to the present invention has a specific surface area of 50 to 100 $m^2/g$, a total pore volume of 0.1 to 0.7 $cm^3/g$, and a pore size of 10 to 100 nm so as to decrease the diffusion resistance of the reactant on the catalyst and to realize efficient catalytic transfer between the reactant and the product during the reaction. The preferred support is composed of spherical particles having a size of 1.0 to 2.0 mm, and is commercially available (made by BASF, Germany). In the present invention, the term "sponge-type support" refers to a support having meso/macro pore sizes, and particularly, to a support that has a pore size of 10 to 100 nm and is commercially prepared through an oil dropping process, a granulation process, or a nuclear growth process. Preferably, the crystal phase of alumina according to the present invention includes a gamma, theta or alpha phase, but an alpha phase and a theta phase, characterized by large pore size, are particularly useful. In the case where a gamma phase having a small pore size is used, the retention time of the reactant or product in the support may increase due to the presence of micro- or nano-sized pores therein, thus causing side reactions, undesirably lowering the selectivity and the catalytic activity.

In the present invention, the active metal components for the dehydrogenation catalyst are composed of an alkali metal or an alkaline earth metal and a halogen, as well as platinum and tin. Based on the total weight of the catalyst, platinum is loaded in an amount of 0.2 to 0.5 wt %, and preferably 0.2 to 0.3 wt %, tin is loaded in an amount of 0.2 to 1.0 wt %, and preferably 0.4 to 0.6 wt %, and the alkali metal or alkaline earth metal is loaded in an amount of 0.2 to 0.8 wt %, and preferably 0.4 to 0.5 wt %, provided that the weight ratio of tin relative to platinum falls in the range of 2.0 to 2.5, and the weight ratio of alkali metal or alkaline earth metal falls in the range of 2 to 3. If the amount of platinum is low, the conversion efficiency is decreased. On the other hand, if the amount thereof is too high, many side reactions may occur, undesirably lowering selectivity.

For the above catalyst, platinum is used as a main metal, tin is used as an assistant metal, and the alkali metal or alkaline earth metal includes any metal selected from the group consisting of potassium, lithium, and sodium. The halogen is selected from the group consisting of chlorine, phosphorus, and fluorine. Individual metal components have different functions, but are generally referred to using the comprehensive term "active metal" or "active composite metal".

The process for impregnating the sponge-type support with the active metal is not particularly limited so long as it is typically useful in the related field, and may be specifically performed in a manner such that an active metal is dissolved in a solvent and is then loaded through incipient wetness impregnation or excess impregnation.

In the step of dissolving the active metal in the solvent during the process for impregnating the sponge-type support with the active metal, an alumina sol is added to the solvent, thereby enhancing the adhesion of the loaded active metal to the support. The amount of the alumina sol that is added is 0.5 to 5%, and preferably 1 to 2%, based on the total volume of the solvent.

In the present invention, the thermal treatment temperature of the support having the loaded active metal falls in the range of 400 to 700° C., and preferably 450 to 500° C. Particularly useful is 470° C. If the thermal treatment temperature is lower than 400° C., the loaded metal may not be converted into a metal oxide species. On the other hand, if the thermal treatment temperature is higher than 700° C., intermetallic aggregation may occur, with the result that the activity of the catalyst is not high relative to the amount of the catalyst.

The method of the present invention preferably further includes reducing the thermally treated catalyst, that is, the fired catalyst, in a hydrogen atmosphere. Typically, an active species during the dehydrogenation is not a metal oxide species but a reduced metal species, and thus, the reduction process using hydrogen is preferably carried out during the preparation of all catalysts. The reduction process is performed at 400 to 700° C., and most preferably 450° C. If the reduction process is performed at a temperature lower than 400° C., the metal oxide species cannot be completely reduced, and two or more kinds of metal particles may be individually present, rather than being alloyed. On the other hand, if the reduction process is performed at a temperature higher than 700° C., two or more kinds of metal particles may be aggregated and sintered, thereby decreasing the number of active sites and the catalytic activity.

In the present invention, the conversion of the paraffin hydrocarbon into an olefin is carried out in a manner in which a hydrocarbon having 2 to 20 carbon atoms, and preferably 9 to 13 carbon atoms, including paraffin, isoparaffin, or alkyl aromatics, is diluted with hydrogen using the dehydrogenation catalyst according to the present invention, and may undergo a gaseous reaction under conditions of a reaction temperature of 400 to 600° C., and preferably 470° C., a pressure of 0 to 2 atm, and preferably 1.6 atm, with a liquid hourly space velocity (LHSV) of the paraffin hydrocarbon ranging from 1 to 30 $h^{-1}$, and preferably from 20 to 30 $h^{-1}$. The reactor for producing the olefin through dehydrogenation is not particularly limited, but may be a fixed-bed catalytic reactor configured such that a catalyst is packed in the reactor. Since dehydrogenation is an endothermic reaction, it is important that the catalytic reactor always be adiabatic. In the present invention, it is important that the dehydrogenation be carried out under the condition that the reaction temperature, pressure and LHSV are maintained within appropriate ranges. If the reaction temperature is low, the reaction may not occur. On the other hand, if the reaction temperature is too high, the reaction pressure is proportionally increased, and side reactions, such as coke production, isomerization, etc., may also take place.

A better understanding of the present invention may be obtained through the following examples which are set forth to illustrate, but are not to be construed to limit the present invention.

MODE FOR INVENTION

Example 1: Preparation of Catalyst Using Sponge-Type Alumina Support

A sponge-type alumina support (made by BASF, Germany, specific surface area: 62 $m^2/g$, pore volume: 0.4 $cm^3/g$, average pore size: 13 nm) was impregnated with platinum through incipient wetness impregnation after the dilution of platinum to an amount of 0.2 wt % based on the total weight of the catalyst with deionized water corresponding to the total pore volume of the support, using chloroplatinic acid as a platinum precursor. The platinum-loaded composition was thermally treated at 470° C. for 4 hr in an air atmosphere to thus immobilize the active metal. Thereafter, tin and lithium in respective amounts of 0.5 wt % and 0.45 wt % based on the total weight of the catalyst were loaded into pores of the support through incipient wetness impregnation, and the resulting metal-loaded composition was thermally treated at 470° C. in an air atmosphere, thereby preparing a metal-loaded catalyst.

Example 2: Preparation of Catalyst Using Sponge-Type Alumina Support and Alumina Sol An active composite metal-loaded catalyst was prepared in the same manner as in Example 1, with the exception that, when the sponge-type alumina support (made by BASF, Germany, specific surface area: 62 $m^2/g$, pore volume: 0.4 $cm^3/g$, average pore size: 13 nm) was impregnated with platinum, tin and lithium, an alumina sol (2% of the volume of deionized water) was added to deionized water corresponding to the total pore volume of the support.

Comparative Example 1: Preparation of Catalyst Using Alumina Support Having Enlarged Pore Size Through Thermal Treatment An active composite metal-loaded catalyst was prepared in the same manner as in Example 1, with the exception that a support having an enlarged pore size, resulting from firing a typically useful gamma alumina (made by SASOL, Germany) at 1100° C., was used.

Comparative Example 2: Preparation of Catalyst Using Gamma Alumina Support

A metal-loaded catalyst was prepared in the same manner as in Example 1, with the exception that a typically useful gamma alumina (made by SASOL, Germany) was used as the support.

Test Example 1: Evaluation of Performance of Catalyst

In order to measure the activity of the catalyst, a dehydrogenation reaction was carried out. As such, a fixed-bed reaction system was used as the reactor. Specifically, a tubular reactor was packed with 1.16 g of the catalyst, and hydrogen gas was allowed to flow at a rate of 235 cc/min to reduce the catalyst at 470° C. for 1 hr. Subsequently, the temperature of the reactor was maintained constant at 470° C., which was the reaction temperature, after which the paraffin hydrocarbon feed having 9 to 13 carbon atoms was uniformly and continuously fed into the reactor at a rate of 0.7 ml/min using an HPLC pump, and LHSV was fixed to 21 $h^{-1}$. The reaction pressure was maintained constant at 1.6 atm using a pressure controller. The material resulting from the reaction was subjected to quantitative analysis using liquid chromatography. The produced olefin conversion and the olefin selectivity were calculated as follows.

Paraffin conversion=[mol number of paraffin before reaction−mol number of paraffin after reaction]/ [mol number of paraffin before reaction]×100

Olefin selectivity=[mol number of olefin of product]/ [mol number of product]×100%   Equation 1

TABLE 1

| No. | Average pore size of support (nm) | Paraffin conversion (%) | Mono-olefin selectivity (%) | Di-olefin selectivity (%) | Olefin yield (%) |
|---|---|---|---|---|---|
| Ex. 1 | 13 | 17.8 | 87.4 | 7.8 | 16.9 |
| Ex. 2 | 13 | 18.2 | 85.7 | 7.2 | 16.8 |
| C. Ex. 1 | 14 | 18.1 | 84.1 | 6.9 | 16.5 |
| C. Ex. 2 | 9 | 18.4 | 79 | 6.4 | 15.7 |

The invention claimed is:

1. A method of preparing a catalyst for dehydrogenating paraffin having 9 to 13 carbon atoms, comprising:

providing a sponge-type alpha alumina support having meso/macro pores that are connected to each other;

thermally treating the support at 800 to 1200° C. for 2 to 10 hr in an air atmosphere;

diluting platinum, tin and lithium with a volume of deionized water that corresponds to a total pore volume of the support to create a diluted solution;

adding a volume of alumina sol equal to 2% of the volume of deionized water to the diluted solution;

impregnating the platinum, the tin and the lithium of the diluted solution onto the support through incipient wetness impregnation, such that the platinum, tin and lithium are dispersed in the support so as to form a loaded support; and firing the loaded support at 500 to 900° C. for 2 to 10 hr in an air atmosphere to form the catalyst.

2. The method of claim 1, further comprising reducing the catalyst at 400 to 700° C. in a hydrogen atmosphere, after the firing the loaded support.

3. The method of claim 1, wherein the sponge-type alumina support comprises two kinds of pores having a meso pore size and a macro pore size.

4. The method of claim 1, wherein the sponge-type alumina support has a specific surface area of 50 to 100 m$^2$/g, a total pore volume of 0.1 to 0.7 cm$^3$/g, and a pore size of 10 to 100 nm.

* * * * *